United States Patent
Green

(10) Patent No.: US 10,022,255 B2
(45) Date of Patent: Jul. 17, 2018

(54) STENT DELIVERY SYSTEM HAVING ANISOTROPIC SHEATH

(71) Applicant: IDev Technologies, Inc., Santa Clara, CA (US)

(72) Inventor: Michael L. Green, Pleasanton, CA (US)

(73) Assignee: IDEV TECHNOLOGIES, INC., Santa Clara, CA (US)

( * ) Notice: Subject to any disclaimer, the term of this patent is extended or adjusted under 35 U.S.C. 154(b) by 141 days.

(21) Appl. No.: 15/095,816

(22) Filed: Apr. 11, 2016

(65) Prior Publication Data

US 2017/0290690 A1    Oct. 12, 2017

(51) Int. Cl.
| | | |
|---|---|---|
| *A61F 2/06* | (2013.01) | |
| *A61F 2/966* | (2013.01) | |
| *A61F 2/844* | (2013.01) | |
| *A61F 2/90* | (2013.01) | |
| *A61F 2/95* | (2013.01) | |

(52) U.S. Cl.
CPC .............. *A61F 2/966* (2013.01); *A61F 2/844* (2013.01); *A61F 2/90* (2013.01); *A61F 2002/9517* (2013.01); *A61F 2250/0018* (2013.01)

(58) Field of Classification Search
CPC .. A61F 2/962; A61F 2/966; A61F 2002/9665; A61F 2/2436
See application file for complete search history.

(56) References Cited

U.S. PATENT DOCUMENTS

| | | |
|---|---|---|
| 619,403 A | 2/1899 | Grant et al. |
| 1,947,166 A | 2/1934 | Nydegger |
| 2,162,115 A | 6/1939 | Pauls |
| 4,003,289 A | 1/1977 | Yamashita |
| 4,081,885 A | 4/1978 | Shank |
| 4,441,215 A | 4/1984 | Kaster |
| 4,469,101 A | 9/1984 | Coleman et al. |
| 4,655,771 A | 4/1987 | Wallsten |
| 4,739,762 A | 4/1988 | Palmaz |
| 4,776,337 A | 10/1988 | Palmaz |
| 4,954,126 A | 9/1990 | Wallsten |

(Continued)

FOREIGN PATENT DOCUMENTS

| | | |
|---|---|---|
| CA | 2173664 | 10/1996 |
| CA | 2007648 C | 4/2000 |

(Continued)

OTHER PUBLICATIONS

International Search Report, dated Jun. 29, 2017, 3 pages, from PCT/US17/26236.

(Continued)

*Primary Examiner* — Jonathan Miles
*Assistant Examiner* — Wade Miles
(74) *Attorney, Agent, or Firm* — Fulwider Patton LLP

(57) ABSTRACT

A stent delivery system and methods are described. The stent delivery system can include an elongate outer member defining an outer member lumen through which a self-expanding stent is deliverable. The elongate outer member can include an anisotropic portion and a rigid portion proximal to the anisotropic portion. The anisotropic portion can be radially elastic and longitudinally inelastic. The rigid portion can be radially inelastic and longitudinally inelastic.

7 Claims, 10 Drawing Sheets

(56) References Cited

U.S. PATENT DOCUMENTS

| | | |
|---|---|---|
| 5,035,706 A | 7/1991 | Giantureo et al. |
| 5,372,600 A | 12/1994 | Beyar et al. |
| 5,376,077 A | 12/1994 | Gomringer |
| 5,433,723 A | 7/1995 | Lindenberg et al. |
| 5,433,729 A | 7/1995 | Adams et al. |
| 5,443,496 A | 8/1995 | Schwartz et al. |
| 5,443,499 A | 8/1995 | Schmitt |
| 5,458,615 A | 10/1995 | Klemm et al. |
| 5,464,408 A | 11/1995 | Duc |
| 5,496,277 A | 3/1996 | Termin et al. |
| 5,575,818 A | 11/1996 | Pinchuk |
| 5,618,301 A | 4/1997 | Hauenstein et al. |
| 5,643,339 A | 7/1997 | Kavteladze et al. |
| 5,665,115 A | 9/1997 | Cragg |
| 5,674,227 A | 10/1997 | Freitag |
| 5,683,451 A | 11/1997 | Lenker et al. |
| 5,702,418 A | 12/1997 | Ravenscroft |
| 5,707,376 A | 1/1998 | Kavteladze et al. |
| 5,713,948 A | 2/1998 | Uflacker |
| 5,749,921 A | 5/1998 | Lenker et al. |
| 5,755,769 A | 5/1998 | Richard et al. |
| 5,766,203 A | 6/1998 | Imran et al. |
| 5,772,668 A | 6/1998 | Summers et al. |
| 5,776,142 A | 7/1998 | Gunderson |
| 5,810,871 A | 9/1998 | Tuckey et al. |
| 5,843,158 A | 12/1998 | Lenker et al. |
| 5,873,906 A | 2/1999 | Lau et al. |
| 5,891,130 A | 4/1999 | Palermo et al. |
| 5,925,074 A | 7/1999 | Gingras et al. |
| 5,968,052 A | 10/1999 | Sullivan, III et al. |
| 6,010,530 A | 1/2000 | Goicoechea |
| 6,019,789 A | 2/2000 | Dinh et al. |
| 6,042,588 A | 3/2000 | Munsinger et al. |
| 6,143,022 A | 11/2000 | Shull et al. |
| 6,156,062 A | 12/2000 | McGuinness |
| 6,156,064 A | 12/2000 | Chouinard |
| 6,162,244 A | 12/2000 | Braun et al. |
| 6,174,328 B1 | 1/2001 | Cragg |
| 6,174,329 B1 | 1/2001 | Callol et al. |
| 6,174,330 B1 | 1/2001 | Stinson |
| 6,200,337 B1 | 3/2001 | Moriuchi et al. |
| 6,214,025 B1 | 4/2001 | Thistle et al. |
| 6,231,581 B1 | 5/2001 | Shank et al. |
| 6,241,758 B1 | 6/2001 | Cox |
| 6,248,112 B1 | 6/2001 | Gambale et al. |
| 6,251,135 B1 | 6/2001 | Stinson et al. |
| 6,302,893 B1 | 10/2001 | Limon et al. |
| 6,306,163 B1 | 10/2001 | Fitz |
| 6,336,938 B1 | 1/2002 | Kavteladze et al. |
| 6,340,367 B1 | 1/2002 | Stinson et al. |
| 6,346,118 B1 | 2/2002 | Baker et al. |
| 6,350,277 B1 | 2/2002 | Kocur |
| 6,352,531 B1 | 3/2002 | O'Connor et al. |
| 6,514,261 B1 | 2/2003 | Randall et al. |
| 6,592,614 B2 | 7/2003 | Lenker et al. |
| 6,599,296 B1 | 7/2003 | Gillick et al. |
| 6,626,936 B2 | 9/2003 | Stinson |
| 6,676,693 B1 * | 1/2004 | Belding ............... A61F 2/95 606/108 |
| 6,755,854 B2 | 6/2004 | Gillick et al. |
| 6,792,979 B2 | 9/2004 | Konya et al. |
| 6,837,901 B2 | 1/2005 | Rabkin et al. |
| 6,849,086 B2 | 2/2005 | Cragg |
| 6,866,669 B2 | 3/2005 | Buzzard et al. |
| 6,872,011 B2 | 3/2005 | Ikeda et al. |
| 6,881,221 B2 | 4/2005 | Golds |
| 6,899,727 B2 | 5/2005 | Armstrong et al. |
| 6,918,882 B2 | 7/2005 | Skujins et al. |
| 6,926,732 B2 | 8/2005 | Derus et al. |
| 6,939,352 B2 | 9/2005 | Buzzard et al. |
| 6,974,472 B2 | 12/2005 | Hong et al. |
| 7,018,401 B1 | 5/2006 | Hyodoh et al. |
| 7,048,014 B2 | 5/2006 | Hyodoh et al. |
| 7,052,511 B2 | 5/2006 | Weldon et al. |
| 7,105,016 B2 | 9/2006 | Shiu et al. |
| 7,122,050 B2 | 10/2006 | Randall et al. |
| 7,402,170 B2 | 7/2008 | McCullagh et al. |
| 7,491,224 B2 | 2/2009 | Cox et al. |
| 7,651,521 B2 | 1/2010 | Ton et al. |
| 7,691,124 B2 | 4/2010 | Balgobin |
| 7,766,960 B2 | 8/2010 | Alexander et al. |
| 7,794,489 B2 | 9/2010 | Shumer et al. |
| 7,806,919 B2 | 10/2010 | Bloom et al. |
| 7,857,844 B2 | 12/2010 | Norton et al. |
| 7,867,267 B2 | 1/2011 | Sullivan et al. |
| 7,927,366 B2 | 4/2011 | Pulnev et al. |
| 7,963,987 B2 | 6/2011 | Melsheimer et al. |
| 8,052,739 B2 | 11/2011 | Pulnev et al. |
| 8,133,266 B2 | 3/2012 | Thomas et al. |
| 8,197,528 B2 | 6/2012 | Colgan et al. |
| 8,414,635 B2 | 4/2013 | Hyodoh et al. |
| 8,414,636 B2 | 4/2013 | Nabulsi et al. |
| 8,419,788 B2 | 4/2013 | Sheldon et al. |
| 8,876,881 B2 | 11/2014 | Sheldon et al. |
| 9,023,095 B2 | 5/2015 | Bueche et al. |
| 9,700,448 B2 * | 7/2017 | Snow ............... A61F 2/966 |
| 9,724,222 B2 * | 8/2017 | Lim ............... A61F 2/966 |
| 9,839,541 B2 * | 12/2017 | Costello ............... A61F 2/88 |
| 2002/0038140 A1 | 3/2002 | Yang et al. |
| 2002/0055775 A1 | 5/2002 | Carpentier et al. |
| 2002/0147489 A1 | 10/2002 | Hong et al. |
| 2002/0151933 A1 | 10/2002 | Sheldon |
| 2002/0151955 A1 | 10/2002 | Tran et al. |
| 2002/0183827 A1 | 12/2002 | Derus et al. |
| 2002/0193863 A1 * | 12/2002 | Rourke ............... A61F 2/95 623/1.11 |
| 2003/0040771 A1 | 2/2003 | Hyodoh et al. |
| 2003/0040772 A1 | 2/2003 | Hyodoh et al. |
| 2003/0216803 A1 | 11/2003 | Ledergerber |
| 2004/0049262 A1 | 3/2004 | Obermiller et al. |
| 2004/0098081 A1 | 5/2004 | Landreville et al. |
| 2004/0181239 A1 | 9/2004 | Dorn et al. |
| 2004/0267348 A1 | 12/2004 | Gunderson et al. |
| 2005/0021123 A1 | 1/2005 | Dorn et al. |
| 2005/0081008 A1 | 4/2005 | Gold et al. |
| 2005/0137699 A1 | 6/2005 | Salahieh et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209675 A1 | 9/2005 | Ton et al. |
| 2005/0246010 A1 | 11/2005 | Alexander et al. |
| 2005/0267568 A1 | 12/2005 | Berez et al. |
| 2006/0212105 A1 | 9/2006 | Dorn et al. |
| 2006/0247661 A1 | 11/2006 | Richards et al. |
| 2007/0043420 A1 | 2/2007 | Lostetter |
| 2007/0156223 A1 | 7/2007 | Vaughan |
| 2007/0208350 A1 * | 9/2007 | Gunderson ............... A61F 2/95 606/108 |
| 2008/0234795 A1 | 9/2008 | Snow et al. |
| 2008/0255653 A1 | 10/2008 | Schkolnik |
| 2008/0290076 A1 | 11/2008 | Sheldon et al. |
| 2009/0076587 A1 | 3/2009 | Cully et al. |
| 2009/0105802 A1 | 4/2009 | Henry et al. |
| 2009/0192584 A1 | 7/2009 | Gerdts et al. |
| 2009/0319019 A1 | 12/2009 | Parker |
| 2010/0063573 A1 | 3/2010 | Hijlkema et al. |
| 2010/0145429 A1 | 6/2010 | Dhoke et al. |
| 2010/0256725 A1 | 10/2010 | Rasmussen |
| 2010/0286756 A1 | 11/2010 | Dorn et al. |
| 2011/0166643 A1 | 7/2011 | Pulnev et al. |
| 2011/0190862 A1 | 8/2011 | Bashiri et al. |
| 2011/0230951 A1 | 9/2011 | Cully et al. |
| 2012/0316638 A1 | 12/2012 | Grad et al. |
| 2012/0330342 A1 * | 12/2012 | Jones ............... A61F 2/01 606/194 |
| 2012/0330398 A1 | 12/2012 | Hyodoh et al. |
| 2014/0114389 A1 | 4/2014 | Hyodoh et al. |
| 2015/0081008 A1 | 3/2015 | Sheldon et al. |

(56) References Cited

U.S. PATENT DOCUMENTS

| | | | |
|---|---|---|---|
| 2015/0238337 A1 | 8/2015 | Bueche et al. | |
| 2015/0265444 A1 | 9/2015 | Kitaoka | |

FOREIGN PATENT DOCUMENTS

| | | |
|---|---|---|
| DE | 4420142 | 12/1995 |
| DE | 102005020785 | 11/2006 |
| DE | 102006053748 | 4/2008 |
| EP | 0518839 | 12/1992 |
| EP | 0722700 | 7/1996 |
| EP | 0747021 | 12/1996 |
| EP | 0857471 | 8/1998 |
| EP | 1121911 | 8/2001 |
| EP | 1208816 | 5/2002 |
| EP | 1447058 | 8/2004 |
| EP | 1582178 | 10/2005 |
| EP | 1803423 | 7/2007 |
| JP | S59-500652 | 4/1984 |
| JP | H05-103830 | 4/1993 |
| JP | H05-502179 | 4/1993 |
| JP | H08-24346 | 1/1996 |
| JP | H08-243168 | 9/1996 |
| JP | H09-99095 | 4/1997 |
| JP | 09-276302 | 10/1997 |
| JP | H09-512460 | 12/1997 |
| JP | H10-66730 A | 3/1998 |
| JP | 11-057021 | 3/1999 |
| JP | 2003-000722 | 1/2003 |
| JP | 2004-510490 | 4/2004 |
| JP | 2005-514155 | 5/2005 |
| JP | 2005-342539 | 12/2005 |
| JP | 2006-506201 | 2/2006 |
| JP | 2006-522649 | 5/2006 |
| JP | 2008-536641 | 9/2008 |
| RU | 2012112203 | 5/2006 |
| SU | 1457921 | 2/1989 |
| WO | WO 89/03197 | 4/1989 |
| WO | WO 92/15342 | 9/1992 |
| WO | WO 95/29646 | 11/1995 |
| WO | WO 96/31174 | 10/1996 |
| WO | WO 98/23241 | 6/1998 |
| WO | WO 98/39055 | 9/1998 |
| WO | WO 98/52497 | 11/1998 |
| WO | WO 99/04728 | 2/1999 |
| WO | WO 99/43379 | 9/1999 |
| WO | WO 00/18330 | 4/2000 |
| WO | WO 00/71059 | 11/2000 |
| WO | WO 01/72240 | 10/2001 |
| WO | WO 03/075797 | 9/2003 |
| WO | WO 2004/016201 | 2/2004 |
| WO | WO 2004/091441 | 10/2004 |
| WO | WO 2005/062980 | 7/2005 |
| WO | WO 2006/010177 | 2/2006 |

OTHER PUBLICATIONS

Ashley, The Ashley Book of Knots, pp. 191, 338, 537, 541, 343, 346 (1944).

How to Tie a Bow-Tie, www.cam.ac.uk/societies/cuhags/whitetie/howtotie.htm (3 pages) downloaded Jun. 17, 2011.

"How to Tie a Clove Hitch Knot," eHow, http://www.ehow.com/how_7532_tie-clove-hitch.html (3 pages) downloaded Jun. 17, 2011.

\* cited by examiner

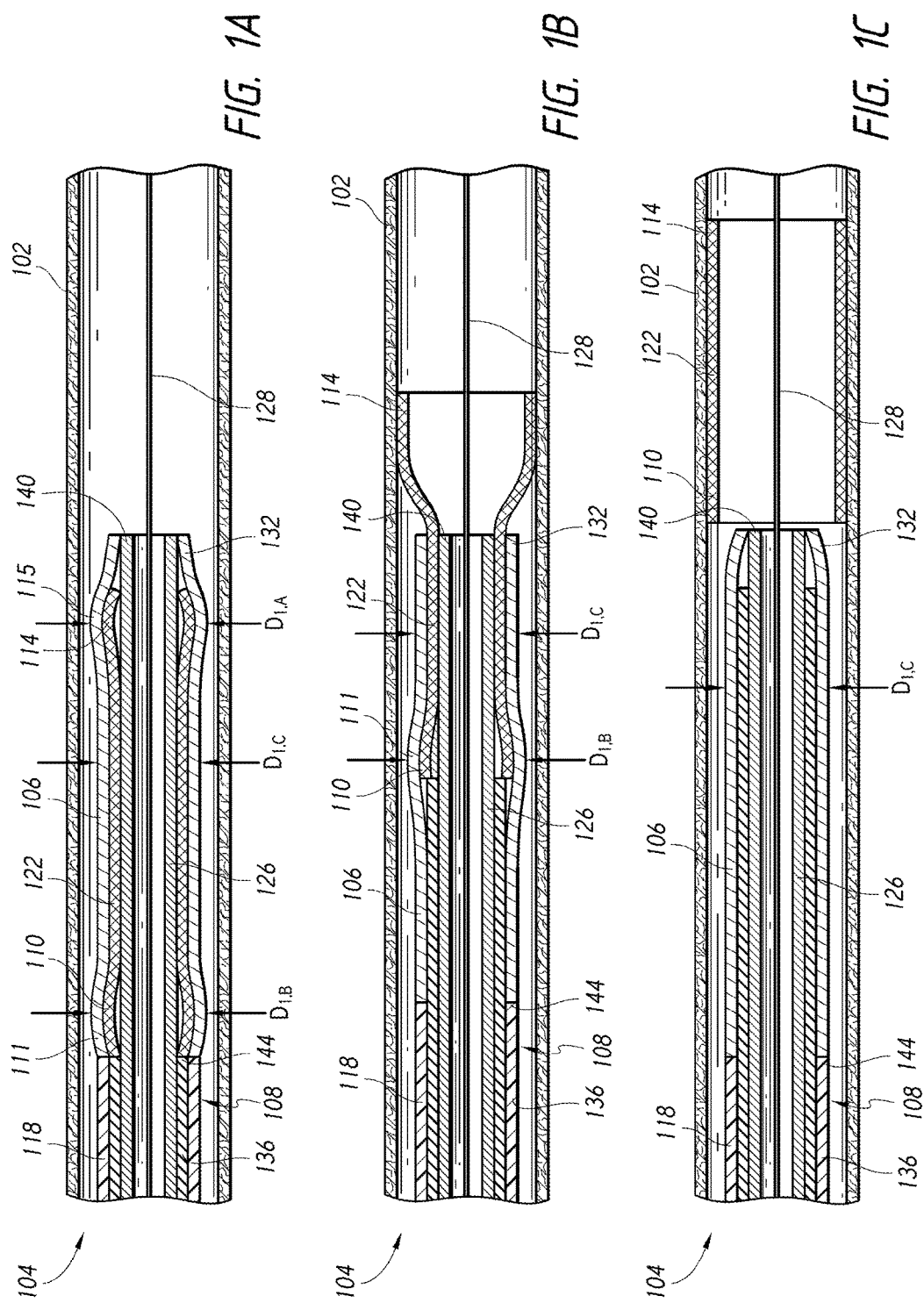

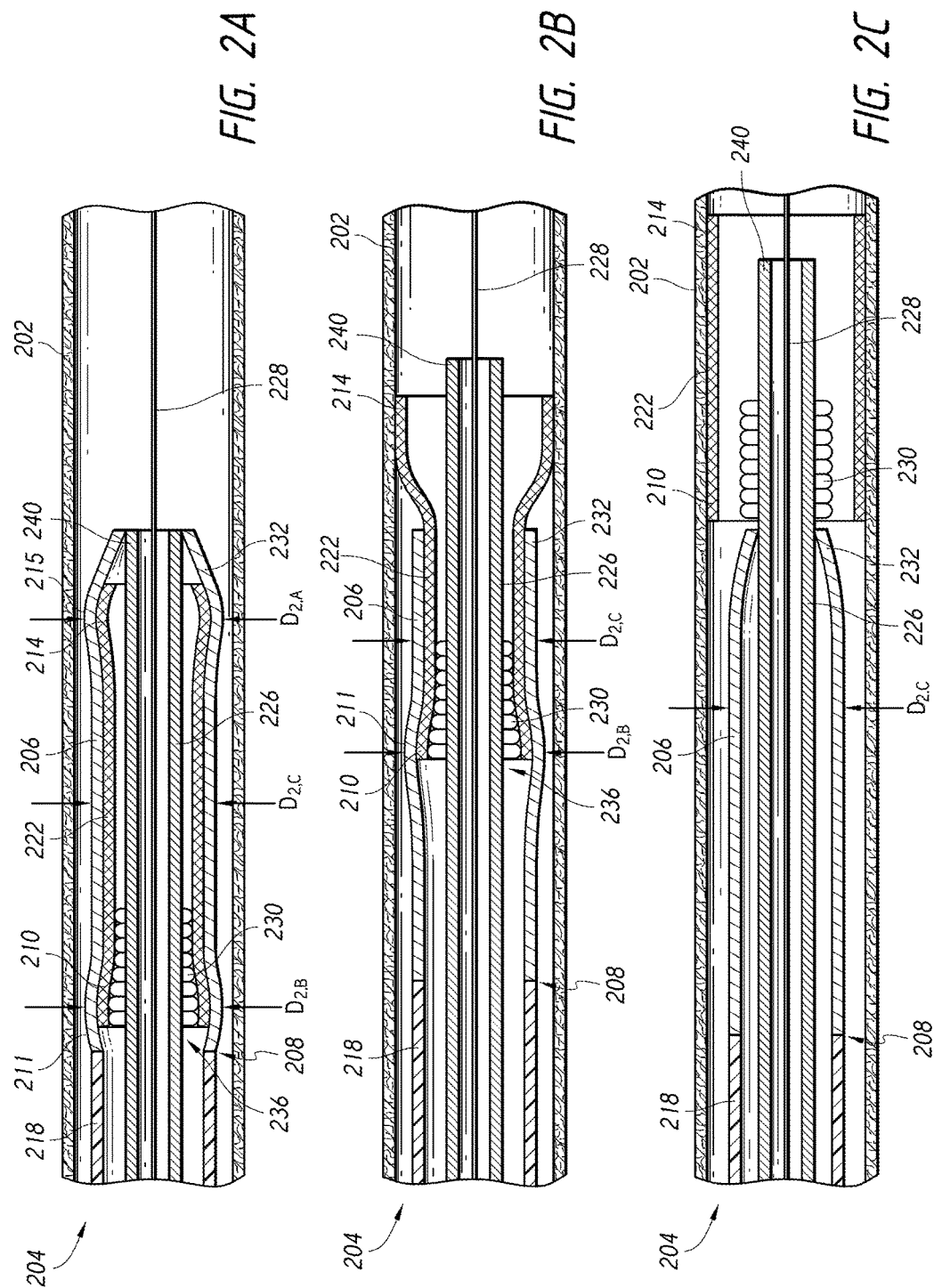

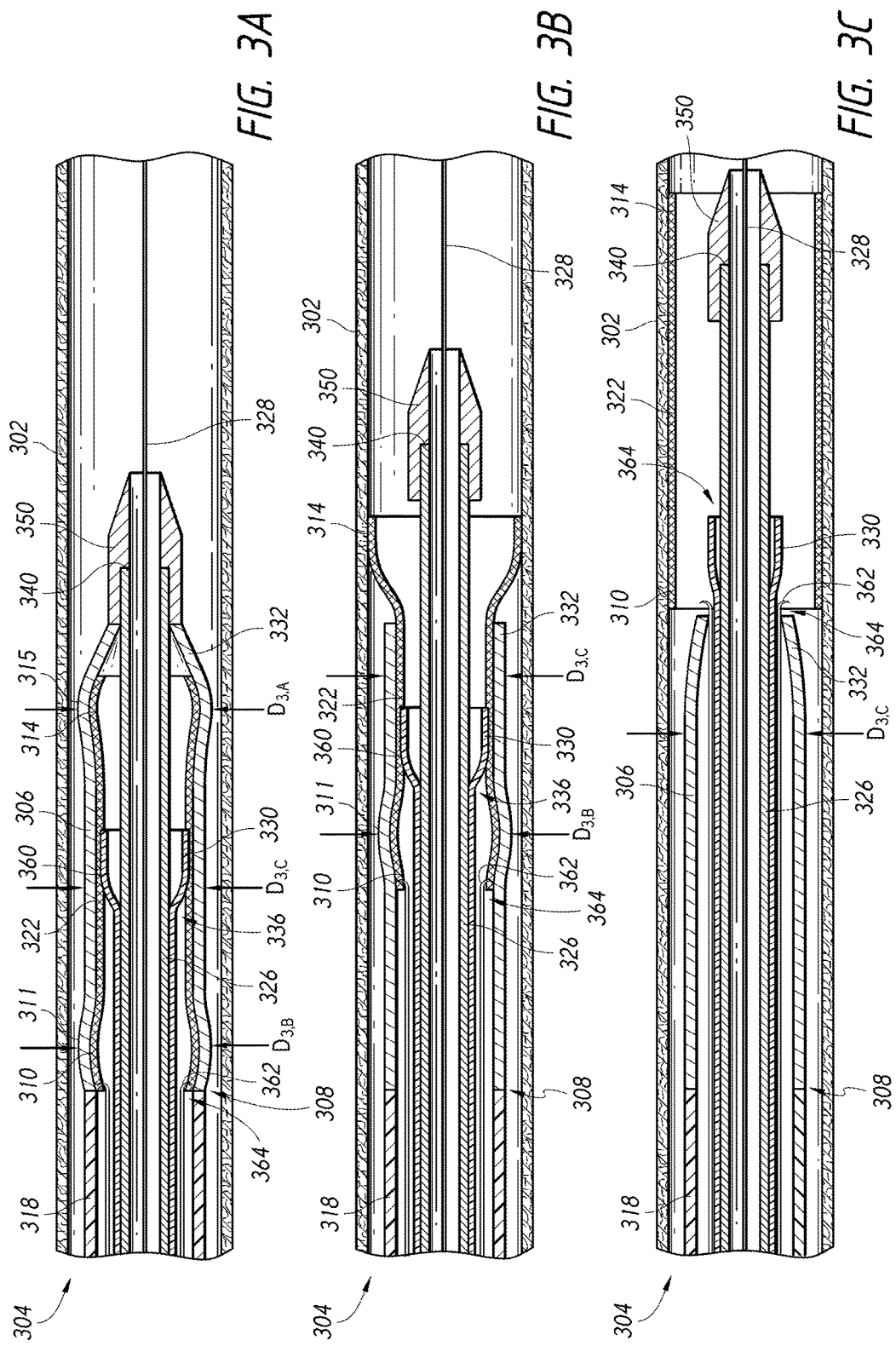

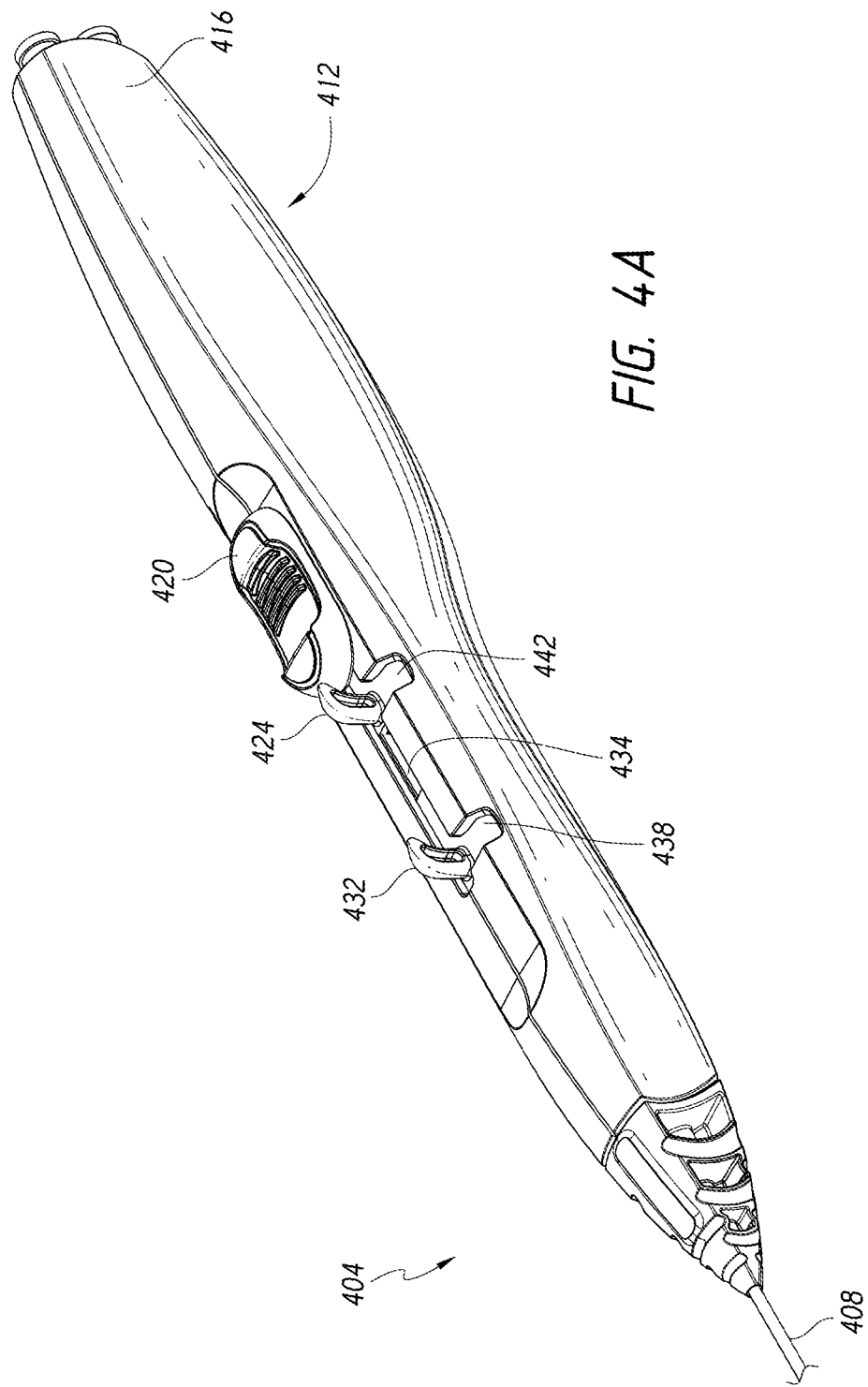

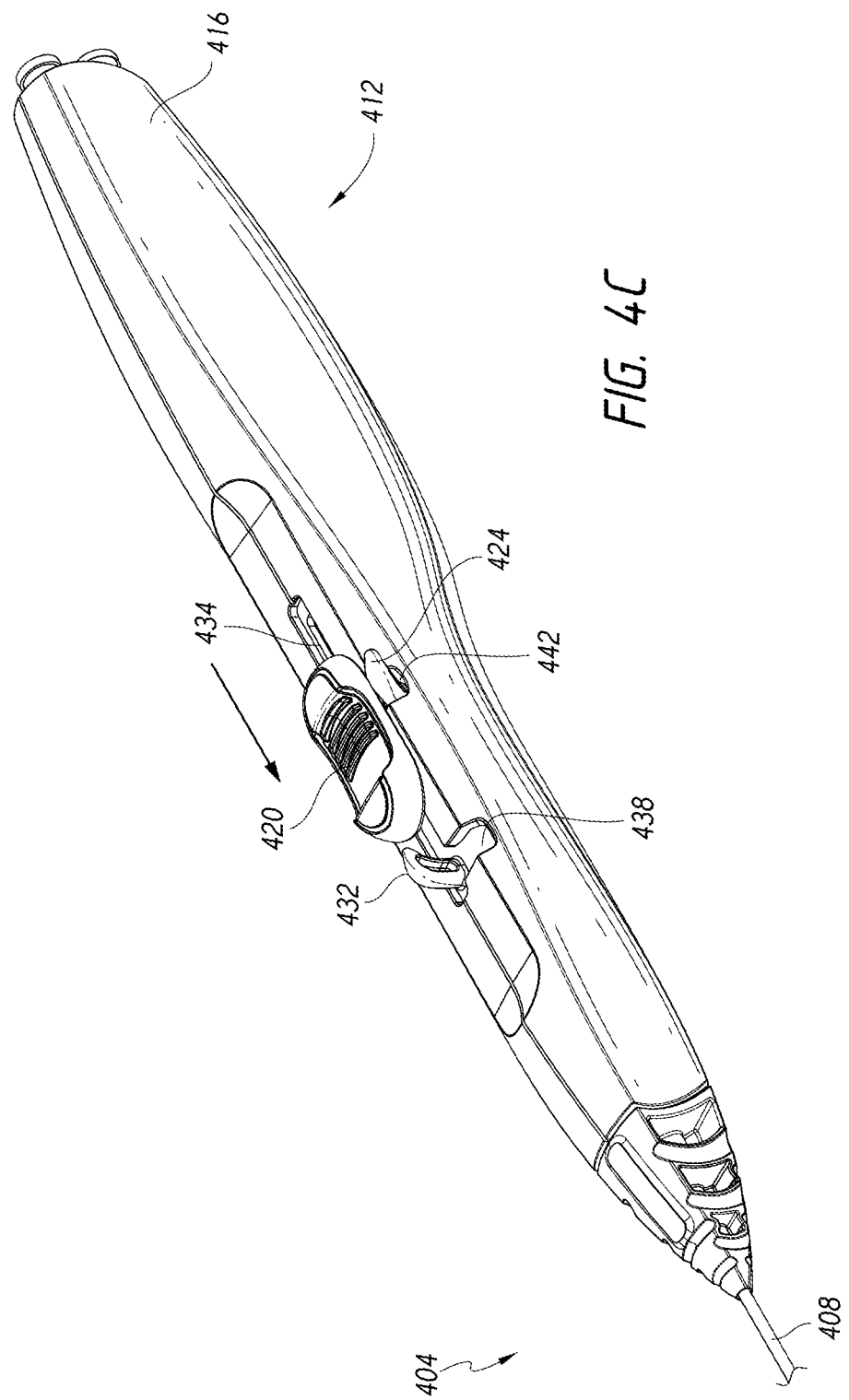

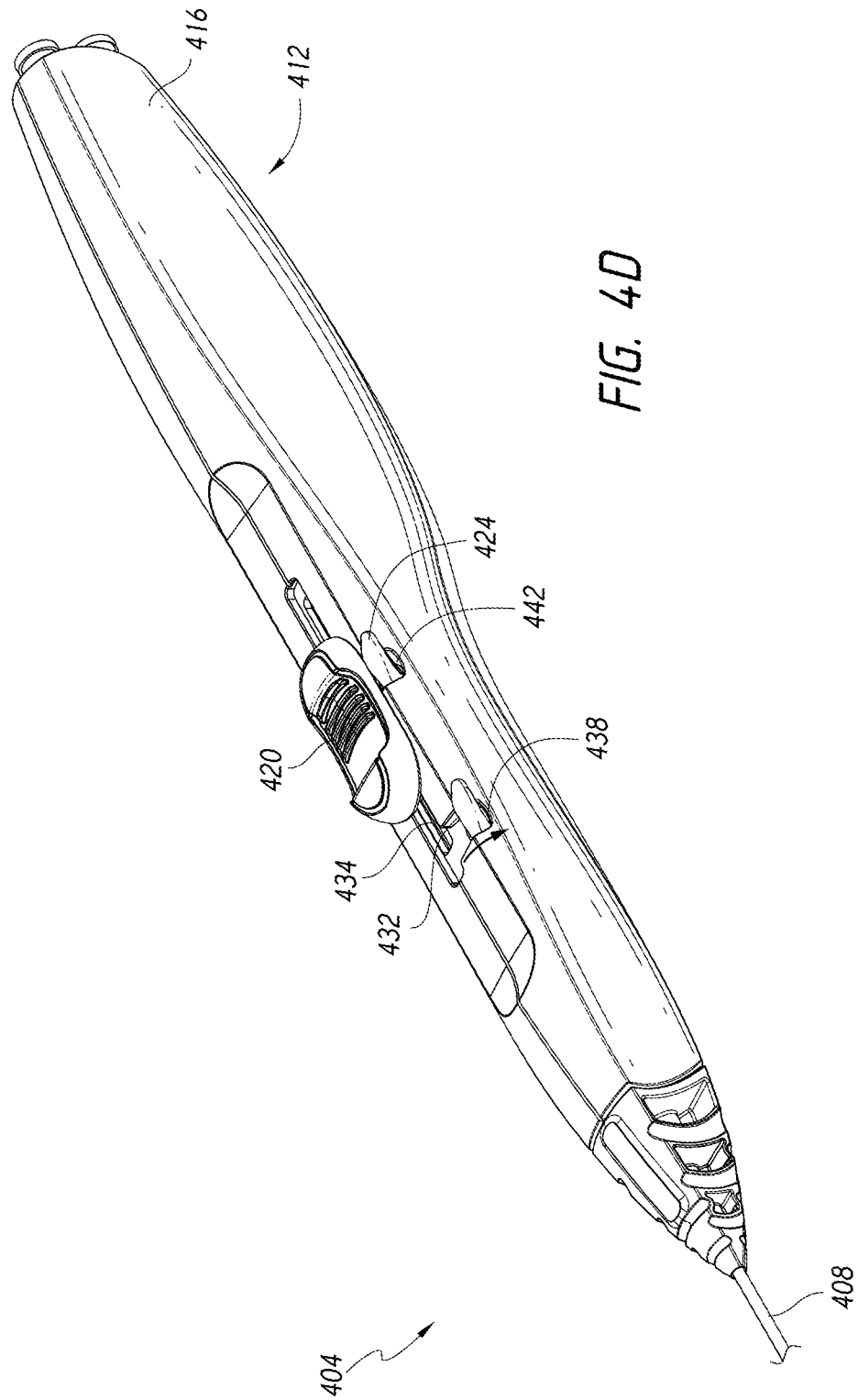

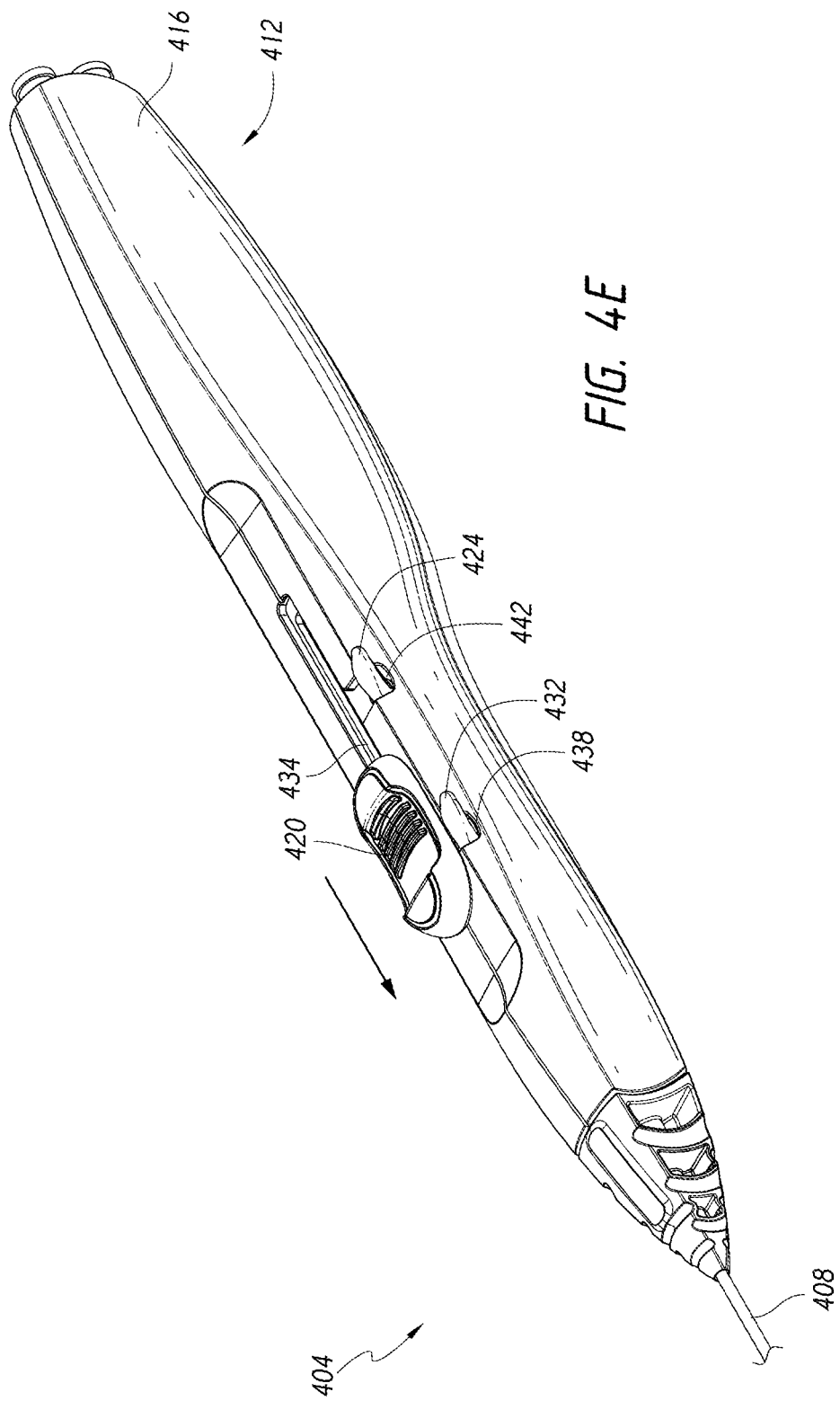

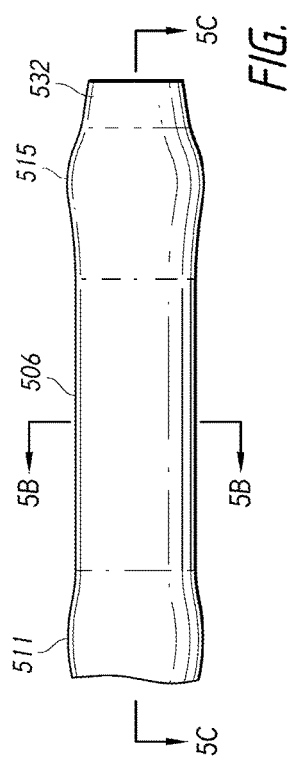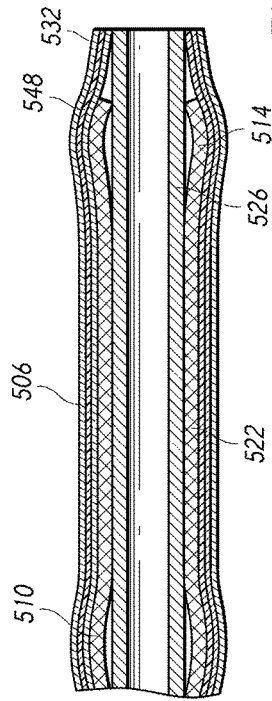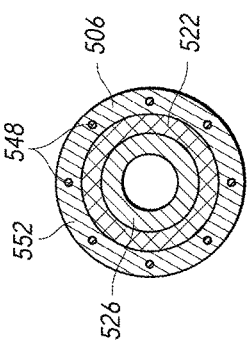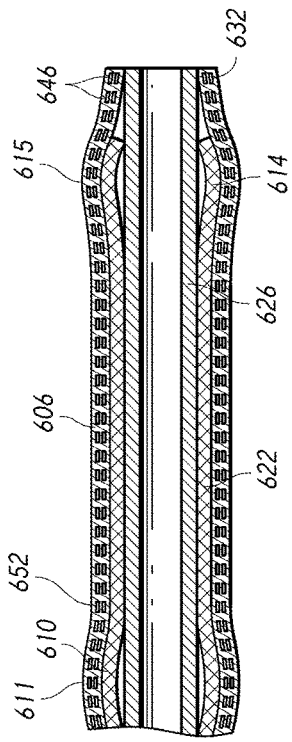

STENT DELIVERY SYSTEM HAVING ANISOTROPIC SHEATH

BACKGROUND

Field

The present disclosure generally relates to devices, systems, methods for making, and methods for use in delivering a stent.

Description of the Related Art

Body vessels or certain non-body structures such as polymer tubes may be at least partially occluded. Stent delivery systems can be used to insert a stent across a lesion or obstruction in order to restore patency to the vessel.

SUMMARY

Traditional delivery systems generally include a rigid, elongate outer member though which a stent is deliverable. However, with a rigid outer member, compression of the stent can be difficult. As a result, when a force is applied to the stent in a longitudinal direction, the stent can buckle radially, which can make delivery of the stent out of the outer member difficult, particularly for longer stents. Thus, the outer member can desirably include an anisotropic portion (e.g., radially elastic and longitudinally inelastic) extending over at least a portion of the stent when the stent is in the outer member. The anisotropic portion can compress the stent such that when a force is applied to the stent in a longitudinal direction, the stent can be more easily pushed out of the outer member. Increasing the ease of delivery can, for example, reduce the total number of user inputs to fully deploy the stent, decrease cost and/or complexity of the delivery system, increase deployment uniformity from user to user and/or device to device, etc. For example, with a single movement of a user-actuatable element (e.g., push, pull, rotation, or otherwise), a longer portion of the stent can be delivered out of the outer member including the anisotropic portion than out of a non-anisotropic outer member provided the same movement.

Some delivery systems can include an atraumatic tip that is separate from the outer member. However, a proximal end of the atraumatic tip often has a same diameter as the outer member. After the stent is deployed, withdrawal of the large, atraumatic tip through the stent may be difficult. Thus, the outer member can desirably include an anisotropic portion (e.g., radially elastic and longitudinally inelastic) to compress the stent to a lower profile to reduce the size of the atraumatic tip. For example, the compressed stent can have an inner diameter sized to only receive a guidewire lumen. The outer member with the anisotropic portion would include a substantially smaller tip than the non-anisotropic outer member. In some embodiments, the anisotropic portion can compress the stent such that a distal end of the stent is tapered. If the guidewire lumen does not extend beyond the distal end of the stent, the delivery system may not include the separate atraumatic tip. Instead, the distal end of the outer member can form the distal end of the delivery system.

Various delivery systems for delivering a stent (e.g., a self-expanding stent) that address the problems discussed above are described herein. In general, the stent delivery system can include an elongate outer member and a pusher assembly in a lumen of the elongate outer member. At least a portion of the elongate outer member can be anisotropic (e.g., a portion or full length). The anisotropic portion can be radially elastic and longitudinally inelastic. When the anisotropic portion only extends along a partial length of the elongate outer member, the elongate outer member can include a rigid portion proximal to the anisotropic portion. The rigid portion can be radially inelastic and longitudinally inelastic.

The above-mentioned stent delivery system may include a guidewire channel positioned radially inward of the elongate outer member. A guidewire may be inserted through the guidewire channel.

In any of the above-mentioned stent delivery systems, a distal portion of the elongate outer member can include longitudinal struts embedded within the wall of the elongate outer member. At least a distal section of each of the longitudinal struts can be biased radially inward to form a tapered distal end of the elongate outer member.

In any of the above-mentioned stent delivery systems, the pusher assembly can include an engagement sleeve positioned radially inward of the elongate outer member and/or radially outward of a guidewire channel (e.g., between a proximal portion of the self-expanding stent and the guidewire channel). The engagement sleeve can be molded to an internal surface of the proximal portion of the self-expanding stent such that the engagement sleeve extends into at least some recesses of the self-expanding stent. The engagement sleeve can be configured to distally advance the self-expanding stent out of the outer member lumen and to proximally retract the self-expanding stent into the outer member lumen.

In any of the above-mentioned delivery systems, the self-expanding stent can be positioned radially inward of the anisotropic portion of the elongate outer member in a compressed configuration in which the stent has flared ends. The anisotropic portion of the elongate outer member can be at least as long as the self-expanding stent in the compressed configuration. Parts of the anisotropic portion can surround the flared ends of the self-expanding stent in the compressed configuration.

Some aspects of the disclosure are directed toward methods of delivering a self-expanding stent using a stent delivery system described herein. The method can include advancing the stent delivery system, for example any of the above-mentioned delivery systems, over a guidewire. The method can include advancing the self-expanding stent out of the elongate outer member and expanding the self-expanding stent from the compressed configuration to an expanded configuration. During advancement of the self-expanding stent out of the elongate member, a diameter of the anisotropic portion can be less than or equal to a diameter of at least one of the parts the anisotropic portion surrounding at least one of the flared ends of the self-expanding stent in the compressed configuration.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 1A-1C schematically illustrate cross-sectional views of a distal portion of an embodiment of a stent delivery system in a method of delivering a stent.

FIGS. 2A-2C schematically illustrate cross-sectional views of a distal portion of another embodiment of a stent delivery system in a method of delivering a stent.

FIGS. 3A-3C schematically illustrate cross-sectional views of a distal portion of yet another embodiment of a stent delivery system in a method of delivering a stent.

FIGS. 4A-4E schematically illustrate perspective views of a proximal portion of an embodiment of a stent delivery system in a method of delivering a stent.

FIG. 5A schematically illustrates a side elevation view of a distal portion of an embodiment of the stent delivery system.

FIG. 5B schematically illustrates a cross-section of the distal portion of the stent delivery system shown in FIG. 5A taken through line 5B-5B.

FIG. 5C schematically illustrates a cross-section of the distal portion of the stent delivery system shown in FIG. 5A taken through line 5C-5C.

FIG. 6 schematically illustrates a cross-sectional view of a distal portion of another embodiment of the stent delivery system.

DETAILED DESCRIPTION

Figure 4B:
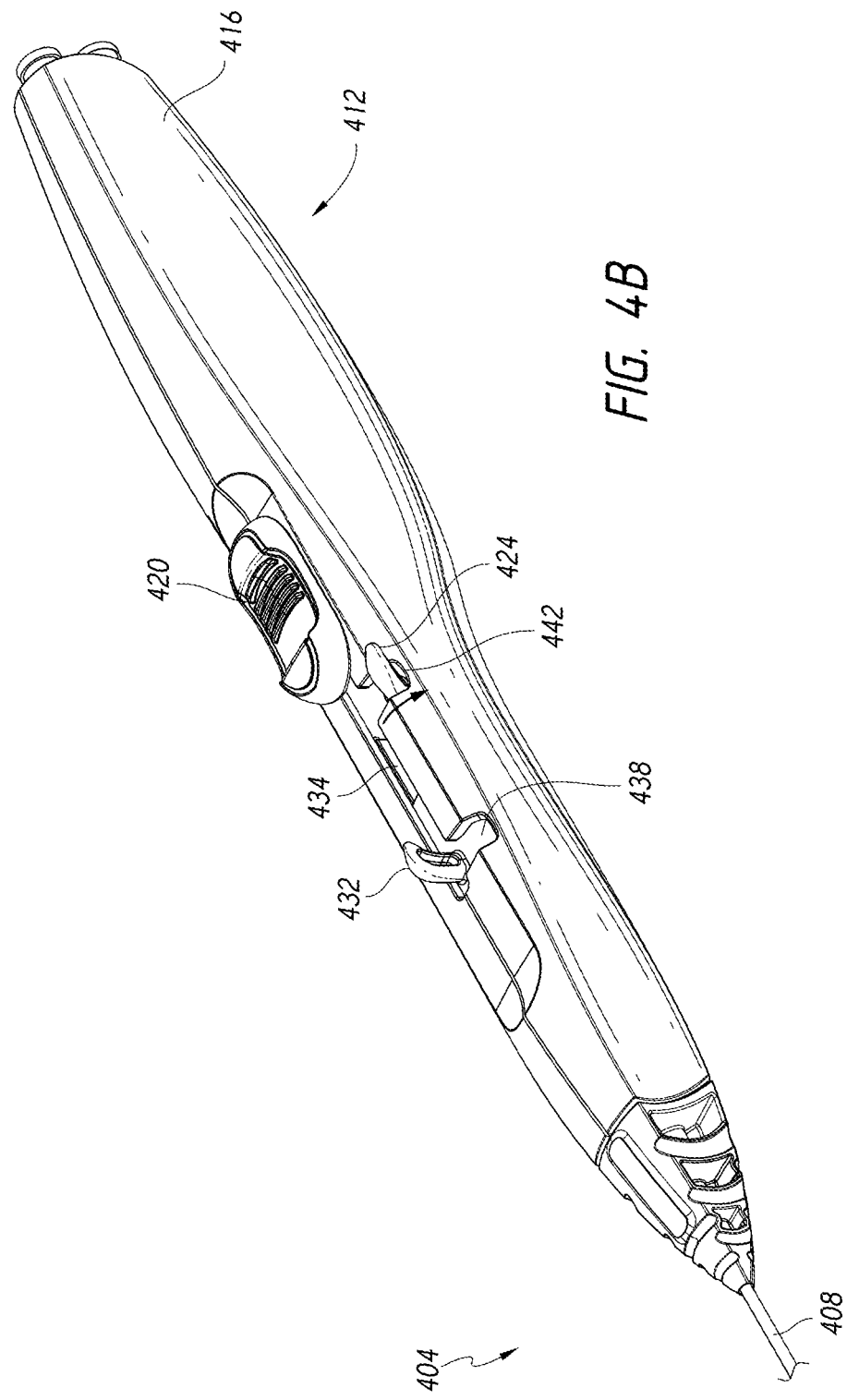

FIGS. 1A-1C illustrate a method of delivering a stent 122 into a vessel 102 (e.g., body vessel or other non-body structure) using a stent delivery system 104. The stent delivery system 104 can include an elongate outer member 108. At least a portion of the outer member 108 (e.g., a portion or a full length) can be anisotropic (e.g., radially elastic and longitudinally inelastic). For example, the outer member 108 can include an anisotropic portion 106 and a rigid portion 118 (e.g., radially inelastic and longitudinally inelastic). As shown in FIGS. 1A-1C, the anisotropic portion 106 can be distal to the rigid portion 118. As another example, the entire outer member 108 can be anisotropic.

The delivery system 104 can optionally include a guidewire channel 126 positioned radially inward of the outer member 108. The guidewire channel 126 at least partially defines a lumen, such that the guidewire channel 126 can be advanced over a guidewire 128. As shown in FIGS. 1A-1C, the distal portion 140 of the guidewire channel 126 extends no further than a distal portion 132 of the anisotropic portion 106. In certain variants, the distal portion 140 of the guidewire channel 126 may extend beyond the distal portion 132 of the anisotropic portion 106, for example to facilitate loading the device onto the guidewire 128.

The delivery system 104 can include a pusher assembly 136 including an elongate inner member. As shown in FIGS. 1A-1C, the pusher assembly 136 can move relative to the guidewire channel 126 and the outer member 108. The pusher assembly 136 can be positioned radially inward from the outer member 108 and/or positioned radially outward from the guidewire channel 126. The pusher assembly 136 can act on (e.g., push or maintain the position of) a proximal portion 110 of the stent 122 (e.g., at or near the proximal end) to advance the stent 122 out of the outer member 108 such that the stent 122 expands from a compressed configuration (see FIG. 1A) in the outer member 108 to an expanded configuration (see FIG. 1C) out of the outer member 108. For example, the pusher assembly 136 can longitudinally advance in the outer member 108 to drive the stent 122 distally out of the outer member 108. In certain variants, the pusher assembly 136 can maintain the position of the stent 122 as the outer member 108 is retracted, or the pusher assembly 136 can drive the stent 122 distally while the outer member 108 is retracted proximally. Advancing the stent 122 distally out of the outer member 108 can be by way of distally driving the pusher assembly 136, proximally retracting the outer member 108, or a combination of the two. That is, the stent 122 may be characterized as being advanced out of the outer member 108 (e.g., beyond the distal portion 132 of the anisotropic portion 106 of the outer member 108) even if the stent 122 does not itself move distally or even moves proximally (e.g., due to foreshortening).

The stent 122 can be positioned in the delivery system 104, radially between the guidewire channel 126 and the outer member 108 (see FIG. 1A). The stent 122 can be positioned in the delivery system 104 when the delivery system 104 is advanced into the vessel 102 or advanced into and through the delivery system 104 after the delivery system 104 is positioned in the vessel 102.

As discussed above, the anisotropic portion 106 can extend across at least a portion of the outer member 108 (e.g., a portion or a full length). For example, the anisotropic portion 106 can extend across at least a portion of the stent 122 when the stent 122 is positioned in the anisotropic portion 106 (e.g., over at least a majority of the length of the stent 122 or over at least the entire length of the stent 122). When the stent 122 is positioned in the delivery system 104, the anisotropic portion 106 can compress the stent 122 to a low profile. For example, the anisotropic portion 106 can compress the stent 122 around the guidewire channel 126 such that an inner diameter of the stent 122 is sized to receive (e.g., to only receive) the guidewire channel 126. If an inner diameter of the guidewire channel 126 is sized to receive a guidewire 128, the inner diameter of the stent 122 may be sized to an outer diameter of the guidewire 128 plus the thickness (difference between inner diameter and outer diameter) of the guidewire channel 126. For example, the inner diameter of the stent may be between about 0.014 inches and about 0.04 inches (e.g., about 0.014 inches, about 0.016 inches, about 0.018 inches, about 0.022 inches, about 0.026 inches, about 0.03 inches, about 0.035 inches, about 0.04 inches, ranges between such values, etc.). In certain variants in which the delivery system 104 does not include the guidewire channel 126, the anisotropic portion 106 can compress the stent 122 such that an inner diameter of the stent 122 is sized to receive (e.g., to only receive) the guidewire 128. If the guidewire channel 126 is omitted, the inner diameter of the stent 122 may be sized to an outer diameter of the guidewire 128. For example, the inner diameter of the stent may be between about 0.01 inches and about 0.04 inches (e.g., about 0.01 inches, about 0.014 inches, about 0.016 inches, about 0.018 inches, about 0.020 inches, about 0.022 inches, about 0.026 inches, about 0.03 inches, about 0.035 inches, about 0.037 inches, about 0.04 inches, ranges between such values, etc.).

The stent 122 can have a proximal portion 110 and a distal portion 114. When the stent 122 is positioned entirely within the anisotropic portion 106, the proximal portion 110 and distal portion 114 of the stent can form flared ends, for example due to end effects of woven stent 122, such that a diameter $D_{1,A}$, $D_{1,B}$ of the parts 111, 115 of the anisotropic portion 106 covering the flared ends, respectively, can be greater than a diameter $D_{1,C}$ of a remaining portion of the anisotropic portion 106 (see FIGS. 1A and 1B). When the proximal portion 110 and the distal portion 114 of the stent 122 have a greater diameter than an intermediate portion of the stent 122, the intermediate portion of the stent 122 can generate less drag to provide less friction during delivery.

Although suitable for deploying several kinds of stents, the systems described herein may be particularly advantageous for self-expanding woven stents such as described in U.S. Pat. No. 7,018,401, filed Feb. 1, 2000, titled "Woven Intravascular Devices and Methods for Making the Same and Apparatus for Delivery of the Same," and U.S. patent application Ser. No. 11/876,666, filed Oct. 22, 2007, titled "Secured Strand End Devices," both of which are hereby incorporated by reference in their entirety. For example, the stent 122 can be a self-expanding stent, for example due to shape-setting of shape memory material such as nitinol. The stent 122 can include a plurality of strands plain woven to form multiple wire intersections. The delivery systems described herein may be particularly advantageous for self-expanding woven stents because, in a compressed configuration, the plurality of strands can be substantially linear such that the stent can be advanced without compressing the stent in a longitudinal direction or causing the stent to buckle radially. As a result, the stent can be advanced with fewer user inputs and increase deployment uniformity from user to user and/or device to device.

In use, a guidewire 128 can be optionally delivered into a target vessel 102. After the guidewire 128 is in position, the delivery system 104 can be advanced over the guidewire 128 (see FIG. 1A). In certain variants, the compressed stent 122 can be delivered to the target vessel 102 without the use of the guidewire 128 (e.g., through the lumen of a catheter).

As shown in FIG. 1A, before deploying the stent 122, the entire stent 122 can be positioned radially inward of the anisotropic portion 106. The parts 111, 115 of the anisotropic portion 106 covering the flared ends of the stent 122 can have a greater diameter than the remainder of the anisotropic portion 106. The distal portion 132 of the anisotropic portion 106 can be tapered down toward the guidewire channel 126, variants of which are described below. As discussed above, the guidewire channel 126 may extend no further than the distal portion 132 of the guidewire channel 126. In certain variants, a distal end of the anisotropic portion 106 may be proximal of a distal end of the guidewire channel 126. The tapered, distal portion 132 of the anisotropic portion 106 can provide an atraumatic end when the delivery system 104 does not include a separate atraumatic tip. Even when the distal portion 132 is tapered, the distal end of the anisotropic portion 106 remains open (e.g., the distal end can have an opening about as large as an outer diameter of the guidewire channel 126) such that a guidewire 128 can be placed or inserted into the delivery system 104 and the delivery system 104 can be advanced over the guidewire 128. If the distal portion 132 of the anisotropic portion 106 were tapered to a closed tip, placing the guidewire 128 into the delivery system 104 would be difficult (e.g., including prying open the closed tip).

As described above, the anisotropic portion 106 can compress the stent 122 such that when the stent 122 is subject to a force in the longitudinal direction, the stent 122 can be pushed out of the outer member 108 with a reduced number of movements of a user-actuatable element (e.g., less than or equal to three, less than or equal to two, etc.). A single movement of a user-actuatable element (see FIGS. 4A-4E) can deliver a longer portion of the stent 122 out of the outer member 108 including an anisotropic portion 106 than is delivered by the same movement but out of a non-anisotropic outer member.

As described above, driving the pusher assembly 136 or other methods can advance the stent 122 beyond the distal portion 132 of the anisotropic portion 106 and into the vessel 102 (see FIG. 1B). As the stent 122 is advanced out of the outer member 108, the distal portion 132 of the anisotropic portion 106 can expand radially outward (see FIG. 1B) due to the radially outward forces imparted by the self-expanding stent 122. The part 111 of the anisotropic portion 106 covering the proximal flared portion 110 of the stent 122 moves distally as the stent 122 is advanced out of the outer member 108.

The stent 122 can be advanced until the proximal portion 110 of the stent 122 is advanced beyond the distal portion 132 of the anisotropic portion 106 and into an expanded configuration (see FIG. 1C). Without the radially outward forces of the flared ends of the stent 122, the anisotropic portion 106, except for the distal portion 132, may be substantially cylindrical, for example having the same outer diameter as the rigid portion 118. Without the radially outward forces of the stent 122, the distal portion 132 of the anisotropic portion 106 may taper radially inward. Although schematically illustrated in FIGS. 1A-1C as being somewhat similar lengths, the stent 122 in the expanded state (FIG. 1C) may be shorter (e.g., 2 to 4 times shorter) than the stent 122 in the compressed state (FIG. 1A) due to foreshortening.

With reference to FIGS. 2A-2C, another illustrative embodiment of a delivery system and method is shown. The delivery system 204 resembles the delivery system 104 discussed above in many respects. Accordingly, numerals used to identify features of the delivery system 104 are incremented by a factor of one hundred (100) to identify like features of the delivery system 204. This numbering convention generally applies to the remainder of the figures. Any component or step disclosed in any embodiment in this specification can be used in other embodiments.

Similar to the delivery system 104, the stent delivery system 204 can include an elongate outer member 208. At least a portion of the outer member 208 (e.g., a portion or a full length) can be anisotropic (e.g., radially elastic and longitudinally inelastic). For example, the outer member 208 can include an anisotropic portion 206 and a rigid portion 218 (e.g., radially inelastic and longitudinally inelastic). As shown in FIGS. 2A-2C, the anisotropic portion 206 can be distal to the rigid portion 218.

The delivery system 204 can include a pusher assembly 236 that can act on a portion of a stent 222 between the proximal and distal ends of the stent 222 (e.g., by engaging wire intersections of a woven stent). For example, the pusher assembly 236 can include a guidewire channel 226 positioned radially inward of the outer member 208. The guidewire channel 226 at least partially defines a lumen, such that the guidewire channel 226 can be advanced over a guidewire 228. As shown in FIG. 2A, initially, the distal portion 240 of the guidewire channel 226 extends no further than the distal portion 232 of the anisotropic portion 206, at least while being advanced in a vessel 202 (e.g., over the guidewire 228). When the distal portion 240 of the guidewire channel 226 extends no further than the distal portion 232 of the anisotropic portion 206, the distal portion 232 of the anisotropic portion 206 can taper down toward the guidewire channel 226, which can be especially useful when the delivery system 204 does not include a separate atraumatic tip. The guidewire channel 226 can be advanced such that the distal portion 240 of the guidewire channel 226 extends beyond the distal portion 232 of the anisotropic portion 206.

As the guidewire channel 226 is advanced out of the anisotropic portion 206, the tapered, distal portion 232 of the anisotropic portion 206 can expand radially outward (see FIG. 2B) due to the radially outward forces imparted by the self-expanding stent 222. Before the distal portion 232 of the anisotropic portion 206 expands radially outward, the anisotropic portion 206 can have a distal opening about as large as an outer diameter of the guidewire channel 226 to facilitate insertion of the guidewire 228 into the delivery system 204.

The stent 222 can be positioned in the delivery system 204, between the guidewire channel 226 and the outer member 208 (see FIG. 2A). The stent 222 can be positioned in the delivery system 204 when the delivery system 204 is advanced into the vessel 202 or advanced into the delivery system 204 after the delivery system 204 is positioned in the vessel 202.

The anisotropic portion 206 can extend across at least a portion of the stent 222 when the stent 222 is positioned in the anisotropic portion 206 (e.g., over at least a majority of the length of the stent 222 or over at least the entire length of the stent 222). When the stent 222 is positioned in the delivery system 204, the anisotropic portion 206 can compress the stent 222 to a low profile. For example, the anisotropic portion 206 can compress the stent 222 around the guidewire channel 226 such that an inner diameter of the stent 222 is sized to receive (e.g., to only receive) the guidewire channel 226. In certain variants in which the delivery system 204 does not include the guidewire channel 226, the anisotropic portion 206 can compress the stent 222 such that an inner diameter of the stent 222 is sized to receive (e.g., to only receive) the guidewire 228.

The stent 222 can have a proximal portion 210 and a distal portion 214. When the stent 222 is positioned entirely within the anisotropic portion 206, the proximal and distal portions of the stent 210, 214 can form flared ends such that a diameter $D_{2,A}$, $D_{2,B}$ of the parts 211, 215 of the anisotropic portion 206 covering the flared ends can be greater than a diameter $D_{2,C}$ of a remaining portion of the anisotropic portion 206 (see FIGS. 2A and 2B). When the proximal portion 210 and the distal portion 214 of the stent 222 have a greater diameter than an intermediate portion of the stent 222, the intermediate portion of the stent 222 can generate less drag to provide less friction during delivery.

The delivery system 204 can include a stent-retention element that allows the operator to retract the stent 222 into the outer member 208, provided that the stent 222 has not been advanced completely out of the outer member 208. For example, as shown in FIGS. 2A-2C, the delivery system 204 can include an engagement sleeve 230 positioned between an internal surface of at least the proximal portion 210 of the stent 222 and the guidewire channel 226 when the stent 222 is in the delivery system 204. The engagement sleeve 230 can be secured to the guidewire channel 226 such that advancement of the guidewire channel 226 also advances the engagement sleeve 230.

The engagement sleeve 230 can engage the proximal portion 210 of the stent 222 as long as the proximal portion 210 of the stent 222 is within the outer member 208. When the proximal portion 210 of the stent 222 is advanced outside of the outer sheath 208, the proximal portion 210 of the stent 222 self-expands to a diameter larger than the engagement sleeve 230. As a result, contact between the stent 222 and the engagement sleeve 230 ceases (see FIG. 2C).

The engagement sleeve 230 can be constructed from a pliable, medical-grade polymer, such as a thermoplastic elastomer (e.g., C-Flex, available from Saint-Gobain Performance Plastics, or FDA Santoprene, available from Exxon Mobil), low-density polyethylene, polyurethane, other soft and/or malleable substances, combinations thereof, and the like. The stent 222 can be nested in the engagement sleeve 230. For example, if the stent 222 is a woven stent, the engagement sleeve 230 will extend into pores between the wire intersections of the stent 222. In some embodiments, after the stent 222 is nested in the engagement sleeve 230 and prior to assembling the delivery system 204, the engagement sleeve 230 can be cured to maintain the geometry of the engagement sleeve 230. When the stent 222 is nested in the engagement sleeve 230, the load is distributed over a broader area of the stent (e.g., around an entire circumference of the stent) to reduce radially outward forces and drag acting on the sheath, such that less delivery force is required to deploy the stent 222 than, for example, only acting on the proximal end of the stent 222.

In use, a guidewire 228 can be optionally delivered into a target vessel 202. After the guidewire 228 is in position, the delivery system 204 can be advanced over the guidewire 228 (see FIG. 2A). In certain variants, the compressed stent 222 can be delivered to the target vessel 202 without the use of the guidewire 228.

As shown in FIG. 2A, before deploying the stent 222, the entire stent 222 can be positioned radially inward of the anisotropic portion 206. The parts 211, 215 of the anisotropic portion 206 covering the flared ends of the stent 222 can have a greater diameter than the remaining portion of the anisotropic portion 206. A distal portion 232 of the anisotropic portion 206 can be tapered down toward the guidewire channel 226.

As described above, the anisotropic portion 206 can compress the stent 222 such that when the stent 222 is subject to a force in the longitudinal direction, the stent 222 can be pushed out of the outer member 208 with a reduced number of movements of a user-actuatable element (e.g., less than or equal to three, or less than or equal to two, etc.) and with greater uniformity device to device and/or user to user. A single movement of a user-actuatable element (see FIGS. 4A-4E) can deliver a longer portion of the stent 222 out of the outer member 208 having an anisotropic portion 206 than out of a non-anisotropic outer member.

Advancing the guidewire channel 226 can advance the stent 222 (e.g., by distally driving the stent 222 or variants thereof) beyond the distal portion 232 of the anisotropic portion 206 and into the vessel 202 (see FIG. 2B). As the guidewire channel 226 moves distally, the engagement sleeve 230 moves distally so that the stent 222 can be advanced out of the outer member 208. As the stent 222 is advanced out of the outer member 208, the distal portion 232 of the anisotropic portion 206 can expand radially outward (see FIG. 2B). The part 211 of the anisotropic portion 206 covering the proximal flared portion 210 of the stent 222 moves distally as the stent 222 is advanced out of the outer member 208. If the stent 222 is improperly deployed or in the wrong position, the stent 222 can be retracted back into the outer member 208 using the engagement sleeve 230, the delivery system 204 repositioned, and the stent 222 re-advanced using the engagement sleeve 230, provided that the stent 222 has not been deployed completely out of the outer member 208 such that the engagement sleeve 230 continues to engage the stent 222.

The stent 222 can be advanced until the proximal portion 210 of the stent 222 is advanced beyond the distal portion 232 of the anisotropic portion 206 and into an expanded configuration (see FIG. 2C). When the proximal portion 210 of the stent 222 is advanced outside of the outer sheath 208, the proximal portion 210 of the stent 222 expands to a diameter larger than the engagement sleeve 230.

Figure 7:
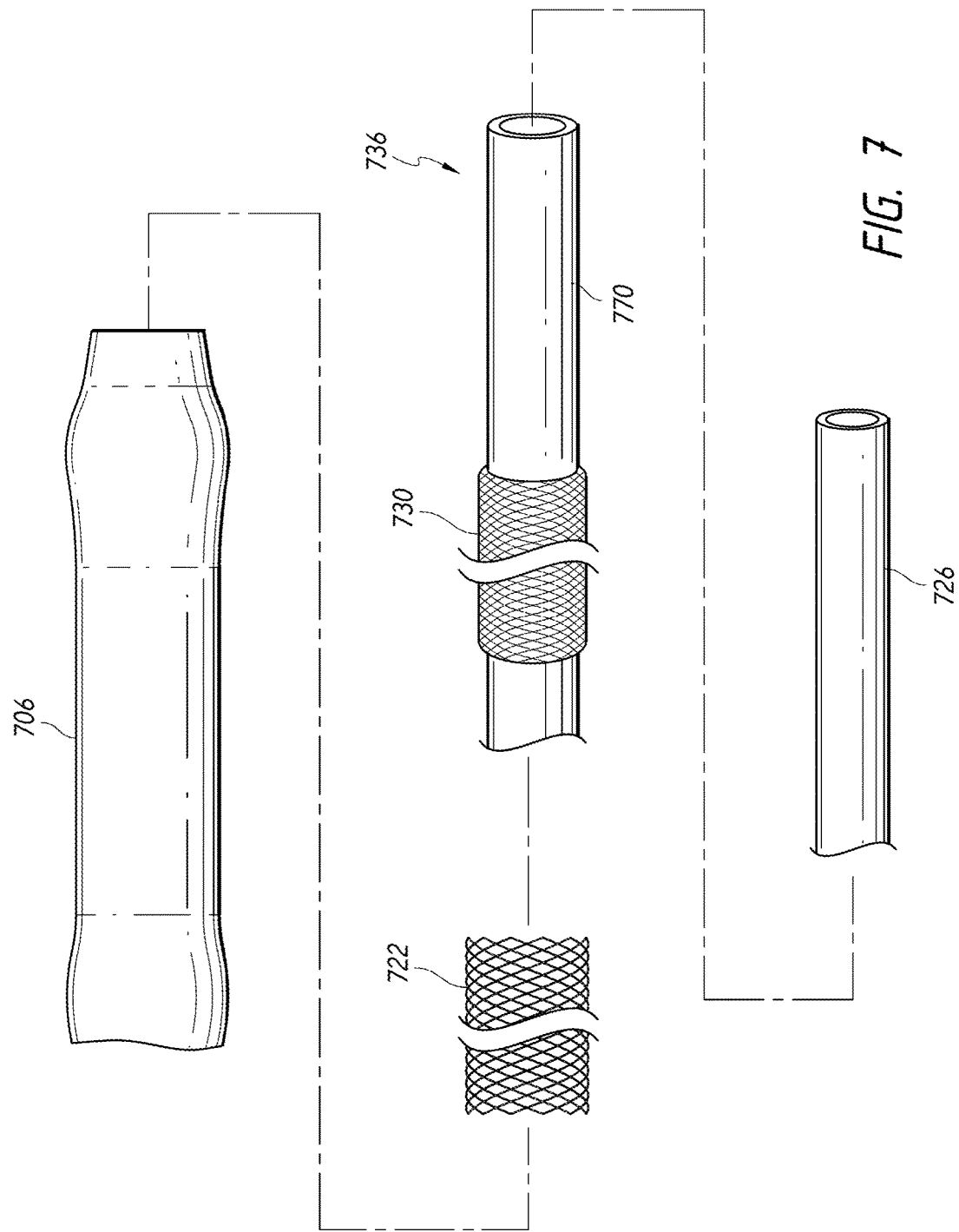
FIG. 7 schematically illustrates a partial exploded view of the distal portion of yet another delivery system.

In certain variants, the pusher assembly 236 can include an elongate member, separate from the guidewire channel 226, that carries the engagement sleeve 230. For example, as shown in FIG. 7, the pusher assembly 736 can include an elongate member 770 that carries the engagement sleeve 730. The elongate member 770 can be positioned radially outward of the guidewire channel 726 and can move relative to the guidewire channel 726 (e.g., in telescoping relation). The elongate member 770 can be positioned radially inward of the anisotropic portion 706 of an outer member and radially inward of the stent 722. The engagement sleeve 730 can engage an inner surface of the stent 722 when at least a proximal portion of the stent 722 is positioned in the anisotropic portion 706.

With reference to FIGS. 3A-3C, another illustrative embodiment of a delivery system is shown. The delivery system 304 resembles the delivery system 104 discussed above in many respects. Accordingly, numerals used to identify features of the delivery system 104 are incremented by a factor of two hundred (200) to identify like features of the delivery system 304. This numbering convention generally applies to the remainder of the figures. Any component or step disclosed in any embodiment in this specification can be used in other embodiments.

Similar to the delivery system 104, the stent delivery system 304 can include an elongate outer member 308. At least a portion of the outer member 308 (e.g., a portion or a full length) can be anisotropic (e.g., radially elastic and longitudinally inelastic). For example, the outer member 308 can include an anisotropic portion 306 and a rigid portion 318 (e.g., radially inelastic and longitudinally inelastic). As shown in FIGS. 3A-3C, the anisotropic portion 306 can be distal to the rigid portion 318.

A stent 322 can be positioned in the delivery system 304, between the guidewire channel 326 and the outer member 308 (see FIG. 3A). The stent 322 can be positioned in the delivery system 304 when the delivery system 304 is advanced into the vessel 302 or advanced into the delivery system 304 after the delivery system 304 is positioned in the vessel 302.

The delivery system 304 can include a pusher assembly 336 that can act on a portion of the stent 322 between the proximal and distal ends of the stent 322 (e.g., by engaging wire intersections of a woven stent). For example, as shown in FIGS. 3A-3C, the pusher assembly 336 can include a guidewire channel 326 positioned radially inward of the outer member 308. The pusher assembly 336 can include a stent-engaging member 360 positioned at a distal portion of the guidewire channel 326. The stent-engaging member 360 can be positioned radially inward from the stent 322. A distal portion of the stent-engaging member 360 can extend radially outward from a proximal portion of the stent-engaging member 360, such that the distal portion of the stent-engaging member 360 can engage the stent 322 (e.g., between wire intersections of a woven stent). The stent-engaging member 360 can move the stent 322 when distally advanced, for example by engaging wire intersections, and not move the stent 322 when proximally retracted, for example by folding inwardly. Multiple engagements of the stent 322 by the stent-engaging member 360 are possible. Additional information regarding stent-engaging members can be found in U.S. patent application Ser. No. 11/876,764, filed Oct. 22, 2007, titled "Devices for Stent Advancement," and U.S. application Ser. No. 13/118,325, filed May 27, 2011, titled "Stent Delivery System with Pusher Assembly," both of which are hereby incorporated by reference in their entirety.

The delivery system 304 can optionally include an atraumatic tip 350 that can be tapered toward its distal end (e.g., generally conical or frustoconical). The atraumatic tip 350 can be positioned at the distal end of the delivery system 304 when the delivery system 304 is advanced into the vessel 302. For example, the atraumatic tip 350 can be connected to a distal portion of the guidewire channel 326 and positioned distal to the distal portion 332 of the anisotropic portion 306. The atraumatic tip 350 can include a tip lumen therethrough, for example in fluid communication with a lumen of the guidewire channel 326, so that the atraumatic tip 350 and the delivery system 304 can be advanced over the guidewire 328. The outer member 308 with the anisotropic portion 306 would include a substantially smaller diameter tip 350 than a non-anisotropic outer member. As such, retraction of the atraumatic tip 350 through the stent 322 can be easier than larger diameter tips that might be used with other delivery systems.

The delivery system 304 can optionally include a stent-retention element 364 that allows the operator to retract the stent 322 into the outer member 308, provided that the stent 322 has not been advanced completely out of the outer member 308. The stent-retention element 364 can be positioned radially outward of the guidewire lumen 326 and radially inward of a proximal portion of the stent 322 (e.g., the flared proximal portion 310) when the stent 322 is in the delivery system 304. For example, as shown in FIGS. 3A-3C, the stent retention element 364 can include one or more hooks or radially-projecting prongs 362 that can engage the stent 322 (e.g., by engaging wire intersections). The radially-projecting prongs 362 are positioned such that the prongs 362 can move with the guidewire channel 326, e.g., secured to the guidewire channel 326 or secured to an elongate inner member that is movable with the guidewire channel 326. Additional information regarding other stent-retention elements can be found in U.S. patent application Ser. No. 11/876,764, filed Oct. 22, 2007, titled "Devices for Stent Advancement," and U.S. application Ser. No. 13/118,325, filed May 27, 2011, titled "Stent Delivery System with Pusher Assembly," both of which are hereby incorporated by reference in their entirety.

In use, a guidewire 328 can be optionally delivered into a target vessel 302. After the guidewire 328 is in position, the delivery system 304 can be advanced over the guidewire 328 (see FIG. 3A). In certain variants, the compressed stent 322 can be delivered to the target vessel 302 without the use of the guidewire 328.

As shown in FIG. 3A, before deploying the stent 322, the entire stent 322 can be positioned radially inward of the anisotropic portion 306. The parts 311, 315 of the anisotropic portion 306 covering the flared ends of the stent 322 can have a greater diameter than the remaining portion of the anisotropic portion 306. A distal portion 332 of the anisotropic portion 306 can be tapered down toward the guidewire channel 326. When the proximal portion 310 and the distal portion 314 of the stent 322 have a greater diameter than an intermediate portion of the stent 322, the intermediate portion of the stent 322 can generate less drag to provide less friction during delivery.

As described above, the anisotropic portion 306 can compress the stent 322 such that when the stent 322 is subject to a force in a longitudinal direction, the stent 322 can be pushed out of the outer member 308 with a reduced number of movements of a user-actuatable actuatable element (e.g., less than or equal to three, less than or equal to two, etc.) or with increased uniformity patient-to-patient or device-to-device. A single movement of a user-actuatable element (see FIGS. 4A-4E) can deliver a longer portion of the stent 322 out of the outer member 308 having an anisotropic portion 306 than out of a non-anisotropic outer member.

Advancing the guidewire channel 326 (e.g., by driving the stent 322 distally or variants thereof) can advance the stent 322 beyond the distal portion 332 of the anisotropic portion 306 and into the vessel 302 (see FIG. 3B). As the guidewire channel 326 moves distally, the stent-engaging member 360 can engage the stent 322 and move the stent 322 distally. If a single user-actuatable movement advances less than an entire length of the stent 322, the stent-engaging element 360 can be proximally retracted. When the stent-engaging element 360 is retracted, the stent-engaging element 360 does not move the stent 322, for example because the stent-engaging element 360 can fold inwardly and slide proximally relative to the stent 322. After retracting the stent-engaging element 360, the stent-engaging element 360 can deliver the stent 322 further out of the outer member 308.

As the stent 322 is advanced out of the outer member 308, the distal portion 332 of the anisotropic portion 306 can expand radially outward (see FIG. 3B). The part 311 of the anisotropic portion 306 covering the proximal flared portion 310 of the stent 322 moves distally as the stent 322 is advanced out of the outer member 308.

If the stent 322 is improperly deployed or in the wrong position, the stent 322 can be retracted back into the outer member 308 using the radially projecting prongs 362, provided that the stent 322 has not been deployed completely out of the outer member 308. Once the proximal portion 310 of the stent 322 is advanced outside of the outer sheath 308, the proximal portion 310 of the stent 322 disengages from the radially projecting prongs 362, thus allowing the stent 322 to expand to a fully expanded configuration (see FIG. 3C). After the stent 322 has been deployed, the atraumatic tip 350 can be retracted through the stent 322 and removed with the stent delivery system 304.

FIGS. 4A-4E illustrate a proximal portion 412 of a delivery system 404 that can be used in connection with any of the above-described delivery systems 104, 204, 304, or variations thereof. The proximal portion 412 can include a handle portion 416 secured to a proximal portion of the outer member 408. The handle portion 416 can include a user-actuatable element 420 that is secured to any one of the above-described pusher assemblies, such that movement of the user-actuatable element 420 moves the pusher assembly. As shown in FIG. 4A-4E, the user-actuatable element 420 can be a sliding member that can traverse a slot 434. Distal movement of the user-actuatable element 420 can advance the pusher assembly, while proximal movement of the user-actuatable element 420 can retract the pusher assembly.

The handle portion 416 can include a number of stoppers (e.g., one, two, etc.) that can limit movement of the user-actuatable element 420. For example, the handle portion 416 can include a distal stopper 432 and a proximal stopper 424. As shown in FIG. 4A, the proximal stopper 424 can limit (e.g., inhibit, prevent) any movement of the user-actuatable element 420 (e.g., during shipment, prior to deploying the stent, etc.). The proximal stopper 424 can be removed or released, e.g., by rotating the proximal stopper 424 into a lateral passage 442 (see FIG. 4B). Although not shown, the proximal stopper 424 can have a passageway through which the user-actuatable element 420 can traverse when the stopper 424 is rotated into the lateral passage 442. The proximal stopper 424 may be biased into the position shown in FIG. 4A, for example by a spring or by a breakable element.

After the proximal stopper 424 has been released, the user-actuatable element 420 can traverse at least a partial length of the slot 434 (see FIG. 4C). The user-actuatable element 420 can move distally or proximally along the partial length of the slot 434 to advance and retract the pusher assembly. A single movement of the user-actuatable element 420 along the partial length of the slot 434 can deliver at least a portion of the stent out of the outer member 408, for example between about 5% and about 95% of a length of the stent (e.g., about 5%, about 10%, about 25%, about 50%, about 75%, about 90%, about 95%, ranges between such values, etc.).

As shown in FIG. 4C, the distal stopper 432 can inhibit or prevent movement of the user-actuatable element 420 along the full length of the slot 434. If the pusher assembly includes a stent retention element, the distal stopper 434 can be useful for preventing unintentional deployment of the proximal end of the stent. The distal stopper 432 may be biased into the position shown in FIG. 4A, for example by a spring or by a breakable element. When the distal stopper 432 is removed or released, e.g., by rotating the distal stopper 432 into a lateral passage 438 (see FIG. 4D), the user-actuatable element 420 can traverse the full length of the slot 434 (see FIG. 4E). Although not shown, the distal stopper 432 can have a passageway through which the user-actuatable element 420 can traverse when the stopper 432 is rotated into the lateral passage 438. When the user-actuatable element 420 traverses the full length of the slot 434, the pusher assembly can push the proximal end of the stent out of the outer member, thereby releasing the stent from the stent retention element (if present) and fully deploying the stent.

FIGS. 5A-5C illustrate an example embodiment of an anisotropic portion 506 of an outer member that can be used with any of the above-described delivery systems 104, 204, 304, 404, or variants thereof. When the stent 522 is positioned in the anisotropic portion 506, the anisotropic portion 506 can compress the stent 522 along the guidewire channel 526. When the anisotropic portion 506 compresses the stent 522, the proximal end 510 and the distal end 514 of the stent 522 form flared ends. When the stent is positioned in the anisotropic portion 506, the diameters of the parts 511, 515 of the anisotropic portion 506 surrounding the proximal end 510 and distal end 514 of the stent 522 are greater than the diameter of the remaining portion of the anisotropic portion 506. The radial elastic properties of the anisotropic portion 506 compress the stent 522 more than a non-anisotropic outer member, while still permitting the flared proximal end 510 of the stent 522 to be delivered through the anisotropic portion 506.

The anisotropic portion 506 can include multiple rigid struts 548 (e.g., two, three, four, five, six, seven, eight, or more). The struts 548 can have a length that is less than or equal to a length of the anisotropic portion 506. Each of the struts 548 can extend longitudinally across an elastic member 552 (e.g., embedded as in FIGS. 5B and 5C, or positioned along an inner and/or outer surface of the elastic member 552). As shown in FIG. 5B, the rigid struts can be positioned around the anisotropic portion 506. For example, the rigid struts 548 can be evenly dispersed around a circumference of the anisotropic portion 506. The struts 548 restrict the longitudinal elasticity of the elastic member 552, while leaving the anisotropic portion 506 sufficiently elastic in the radial direction to compress the stent 522 around the guidewire channel 526.

The elastic member 552 can be constructed from medical grade, elastic materials, such as silicone, low-density polyethylene, polyurethane, PEBAX, combinations thereof and the like. The rigid struts 548 can be constructed from a material that restricts the longitudinal elasticity of the elastic member 552, such as a metal.

When the stent 522 is positioned entirely within the anisotropic portion 506, the distal portion 532 of the anisotropic portion 506 can be tapered. As the stent 522 is delivered out of the anisotropic portion 506, the distal portion 532 of the anisotropic portion 506 can expand radially outward to facilitate delivery of the stent 522 out of the anisotropic portion 506 (see FIGS. 1C, 2C, and 3C).

In other embodiments, as shown in FIG. 6, the anisotropic portion 606 can include a number of fiber 646 (e.g., polyimide fibers, Kevlar, combinations thereof, and the like) embedded within the elastic member 652 (e.g., constructed from silicone, low-density polyethylene, polyurethane, PEBAX, combinations thereof, and the like). The fibers 646 can be distributed such that the anisotropic portion 606 is radially elastic and longitudinally inelastic. For example, each of the fibers 646 can be oriented along a longitudinal direction of the anisotropic portion 606. As shown in FIG. 6, each of the fibers 646 can be a short segment. Multiple fiber segments 646 can be positioned along a length of the anisotropic portion 606 and around a circumference of the anisotropic portion 606. Although not shown, in certain variants, each of the fiber segments 646 can extend along at least a majority of a length of the anisotropic portion 606 (e.g., along substantially the entire length or along the entire length).

When the stent 622 is positioned in the anisotropic portion 606, the anisotropic portion 606 can compress the stent 622 along the guidewire channel 626. The proximal end 610 and the distal end 614 of the stent 622 can form flared ends, such that a diameter of the parts 611, 615 of the anisotropic portion 606 surrounding the ends 610, 614 of the stent 622 is greater than a diameter of the remaining portion of the anisotropic portion 606. The radial elastic properties of the anisotropic portion 606 compress the stent 622 more than a non-anisotropic outer member, while still permitting the flared proximal end 610 of the stent 622 to be delivered through the anisotropic portion 606.

When the stent 622 is positioned entirely within the anisotropic portion 606, the distal portion 632 of the anisotropic portion 606 can be tapered. As the stent 622 is delivered out of the anisotropic portion 606, the distal portion 632 of the anisotropic portion 606 can expand radially outward to facilitate delivery of the stent 622 out of the anisotropic portion 606 (see FIGS. 1C, 2C, and 3C).

Terminology

Although certain delivery systems have been described herein in connection with a plain woven, self-expanding stent, the delivery systems described herein can be used to deliver self-expanding stents or balloon expandable stents having any configuration (e.g., woven, laser cut, or non-plain woven) and constructed from any material (e.g., metal or polymer). For example, in some embodiments, the stent can include a plurality of biodegradable filaments (e.g., made from polyglycolic acid, poly-L-lactic acid, polyorthester, polyanhydride, polyiminocarbonate, or calcium phosphate) woven together to form a self-expanding stent. In some embodiments, the stent can be coated with a drug or the strands can incorporate the drug.

As used herein, the relative terms "proximal" and "distal" shall be defined from the perspective of the delivery system. Thus, proximal refers to the direction of the handle portion of the delivery system and distal refers to the direction of the distal tip.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "advancing the self-expanding stent" include "instructing advancing the self-expanding stent."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 0.01 inches" includes "0.01 inches." Phrases preceded by a term such as "substantially" include the recited phrase and should be interpreted based on the circumstances (e.g., as much as reasonably possible under the circumstances). For example, "substantially linear" includes "linear."

EXAMPLE EMBODIMENTS

The following example embodiments identify some possible permutations of combinations of features disclosed herein, although other permutations of combinations of features are also possible.

1. A method of delivering a self-expanding stent using a stent delivery system, the method comprising:
advancing the stent delivery system over a guidewire, the stent delivery system comprising:
an elongate outer member defining an outer member lumen, the elongate outer member comprising:
an anisotropic portion, the anisotropic portion being radially elastic and longitudinally inelastic, and
a rigid portion proximal to the anisotropic portion, the rigid portion being radially inelastic and longitudinally inelastic;
a guidewire channel positioned radially inward of the elongate outer member, the guidewire insertable into a lumen of the guidewire channel; and
a pusher assembly in the outer member lumen,
wherein the self-expanding stent is positioned radially inward of the anisotropic portion of the elongate outer member in a compressed configuration, the anisotropic portion of the elongate outer member being at least as long as the self-expanding stent in the compressed configuration, the self-expanding stent comprising flared proximal and distal ends in the compressed configuration, parts of the anisotropic portion surrounding the flared ends of the self-expanding stent in the compressed configuration; and
advancing the self-expanding stent out of the elongate outer member, wherein advancing the self-expanding stent out of the elongate outer member comprises expanding the self-expanding stent from the compressed configuration to an expanded configuration,
wherein during advancing the self-expanding stent out of the elongate member, a diameter of the anisotropic portion is less than or equal to a diameter of at least one of the parts the anisotropic portion surrounding at least one of the flared ends of the self-expanding stent in the compressed configuration.

2. The method of Embodiment 1, wherein advancing the self-expanding stent out of the elongate outer member comprises distally advancing the pusher assembly.

3. The method of Embodiment 2, wherein advancing the self-expanding stent further comprises acting on a proximal end of the self-expanding stent.

4. The method of Embodiment 1, wherein advancing the self-expanding stent out of the elongate outer member comprises proximally retracting the elongate outer member and maintaining position of the self-expanding stent using the pusher assembly.

5. The method of Embodiment 1, wherein advancing the self-expanding stent out of the elongate outer member comprises proximally retracting the elongate outer member and distally advancing the pusher assembly.

6. The method of Embodiment 5, wherein proximally retracting the elongate outer member and distally advancing the pusher assembly are at least partially simultaneous.

7. The method of any one of the preceding Embodiments, wherein advancing the self-expanding stent comprises radially expanding an inwardly tapered distal end of the elongate outer member.

8. The method of any one of the preceding Embodiments, wherein the self-expanding stent comprises a plurality of strands plain woven to form multiple wire intersections.

9. The method of Embodiment 8,
wherein the pusher assembly comprises a stent-engaging element positioned radially inward of the self-expanding stent, and
wherein driving the self-expanding stent comprises engaging at least one of the wire intersections of the self-expanding stent between the flared ends of the self-expanding stent when the self-expanding stent is in the compressed configuration.

10. The method of Embodiment 8 or 9, wherein driving the self-expanding stent comprises acting on at least one proximal-most of the wire intersections of the self-expanding stent.

11. The method of any one of the preceding Embodiments, wherein, in the compressed configuration, the self-expanding stent is compressed around the guidewire channel.

12. The method of any one of the preceding Embodiments, wherein the pusher assembly comprises an engagement sleeve positioned between an internal surface of a proximal portion of the self-expanding stent and the guidewire channel, and wherein driving the self-expanding stent comprises driving the engagement sleeve out of the elongate outer member.

13. The method of Embodiment 12, further comprising, before driving the engagement sleeve out of the elongate outer member, retracting the self-expanding stent into the outer member lumen.

14. The method of any one of the preceding Embodiments, further comprising, before driving an entire length of the stent-expanding stent out of the elongate outer member, retracting the self-expanding stent into the outer member lumen using a stent-retention element positioned in the outer member lumen.

15. A stent delivery system comprising:
an elongate outer member defining an outer member lumen through which a self-expanding stent is deliverable, the elongate outer member comprising:
an anisotropic portion, the anisotropic portion being radially elastic and longitudinally inelastic, and
a rigid portion proximal to the anisotropic portion, the rigid portion being radially inelastic and longitudinally inelastic; and
a pusher assembly in the outer member lumen.

16. The stent delivery system of Embodiment 15, wherein a distal end of the elongate outer member forms a distal end of the stent delivery system.

17. The stent delivery system of Embodiment 15 or 16, further comprising a guidewire channel positioned radially inward of at least the anisotropic portion of the elongate outer member.

18. The stent delivery system of any one of Embodiments 15 to 17, further comprising a self-expanding stent configured to self-expand from a compressed configuration when the self-expanding stent is positioned in the outer member lumen to an expanded configuration after the self-expanding stent is advanced out of the elongate outer member.

19. The stent delivery system of Embodiment 18, wherein the self-expanding stent comprises a plurality of strands plain woven to form multiple wire intersections, the self-expanding stent having flared ends when the self-expanding stent is positioned in the outer member lumen.

20. The stent delivery system of Embodiment 19, wherein the pusher assembly comprises a stent-engaging element positioned radially inward of the self-expanding stent and configured to engage at least one wire intersection of the self-expanding stent between the flared ends of the self-expanding stent.

21. The stent delivery system of Embodiment 19, wherein the pusher assembly comprises an engagement sleeve positioned between an internal surface of a proximal portion of the self-expanding stent and the guidewire channel when the self-expanding stent is positioned in the outer member lumen, the engagement sleeve extending between at least some of the wire intersections of the self-expanding stent.

22. The stent delivery system of Embodiment 21, wherein the engagement sleeve is configured to retract the self-expanding stent into the outer member lumen.

23. The stent delivery system of Embodiment 18 or 19 dependent from Embodiment 17, wherein, in the compressed configuration, the self-expanding stent is compressed around the guidewire channel.

24. The stent delivery system of any one of Embodiments 18 to 23, wherein the distal portion of the elongate outer member is at least as long as the self-expanding stent when the self-expanding stent is in the outer member lumen.

25. The stent delivery system of any one of Embodiments 15 to 24, further comprising a stent retention element configured to retract the self-expanding stent into the outer member lumen.

26. A stent delivery system comprising:
an elongate outer member comprising a wall defining an outer member lumen, the elongate outer member comprising a proximal portion and a distal portion, the distal portion comprising longitudinal struts embedded within the wall, at least a distal section of each of the longitudinal struts being biased radially inward to form a tapered distal end of the elongate outer member; and
a pusher assembly positioned in the outer member lumen.

27. The stent delivery system of Embodiment 26, wherein the pusher assembly is configured to drive at least a portion of a stent distally out of the outer member lumen.

28. The stent delivery system of Embodiment 26 or 27, wherein the distal portion of the elongate outer member is more radially flexible than the proximal portion of the elongate outer member.

29. The stent delivery system of any one of Embodiments 26 to 28, further comprising a self-expanding stent configured to self-expand from a compressed configuration when the self-expanding stent is positioned in the outer member lumen to an expanded configuration after the self-expanding stent is advanced out of the elongate outer member by the pusher assembly.

30. The stent delivery system of Embodiment 29, wherein the self-expanding stent is plain woven to form multiple wire intersections.

31. The stent delivery system of Embodiment 30, wherein the pusher assembly comprises a stent-engaging element positioned radially inward of the self-expanding stent and configured to engage at least one wire intersection of the self-expanding stent between ends of the self-expanding stent.

32. The stent delivery system of Embodiment 30, wherein the pusher assembly comprises an engagement sleeve positioned radially inward from the self-expanding stent when the self-expanding stent is positioned in the outer member lumen, the engagement sleeve extending between at least some of the wire intersections of the self-expanding stent.

33. The stent delivery system of Embodiment 32, wherein the engagement sleeve is configured to retract the self-expanding stent into the outer member lumen.

34. The stent delivery system of any one of Embodiments 29 to 33, wherein the distal portion of the elongate outer member is at least as long as the self-expanding stent when the self-expanding stent is in the outer member lumen.

35. The stent delivery system of any one of Embodiments 26 to 34, further comprising a guidewire channel positioned radially inward of at least the distal portion of the elongate outer member.

36. The stent delivery system of any one of Embodiments 26 to 35, further comprising a stent retention element configured to retract the stent into the outer member lumen.

37. A stent delivery system comprising:
an elongate outer member defining an outer member lumen through which a self-expanding stent is deliverable; and
a pusher assembly in the outer member lumen, the pusher assembly comprising an engagement sleeve positioned between the elongate outer member and the guidewire channel and configured to be between a proximal portion of the self-expanding stent and the guidewire channel, the engagement sleeve molded to an internal surface of the proximal portion of the self-expanding stent such that the engagement sleeve extends into at least some recesses of the self-expanding stent, the engagement sleeve configured to distally advance the self-expanding stent out of the outer member lumen and to proximally retract the self-expanding stent into the outer member lumen.

38. The stent delivery system of Embodiment 37, wherein a distal end of the elongate outer member forms a distal end of the delivery system.

39. The stent delivery system of Embodiment 37 or 38, further comprising a guidewire channel positioned radially inward of the elongate outer member.

40. The stent delivery system of any one of Embodiments 37 to 39, further comprising a self-expanding stent configured to self-expand from a compressed configuration when the self-expanding stent is positioned in the outer member lumen to an expanded configuration after the self-expanding stent is advanced out of the elongate outer member.

41. The stent delivery system of Embodiment 40, wherein the self-expanding stent comprises a plurality of strands plain woven to form multiple wire intersections, the self-expanding stent having flared ends when the self-expanding stent is positioned in the outer member lumen.

42. The stent delivery system of Embodiment 40 or 41 dependent from Embodiment 39, wherein, in the compressed configuration, the self-expanding stent is compressed around the guidewire channel.

43. The stent delivery system of any one of Embodiments 37 to 42, wherein a distal portion of the elongate outer member tapers down to the guidewire channel.

The following is claimed:
1. A method of delivering a self-expanding stent using a stent delivery system, the method comprising:
advancing the stent delivery system over a guidewire, the stent delivery system comprising:
an elongate outer member defining an outer member lumen, the elongate outer member comprising:

an anisotropic portion, the anisotropic portion being radially elastic and longitudinally inelastic, and a rigid portion proximal to the anisotropic portion, the rigid portion being radially inelastic and longitudinally inelastic;

a guidewire channel positioned radially inward of the elongate outer member, the guidewire insertable into a lumen of the guidewire channel; and a pusher assembly in the outer member lumen, wherein the self-expanding stent is positioned radially inward of the anisotropic portion of the elongate outer member in a compressed configuration, the anisotropic portion of the elongate outer member being at least as long as the self-expanding stent in the compressed configuration, the self-expanding stent comprising flared proximal and distal ends in the compressed configuration, parts of the anisotropic portion surrounding the flared ends of the self-expanding stent in the compressed configuration; and advancing the self-expanding stent out of the elongate outer member, wherein advancing the self-expanding stent out of the elongate outer member comprises expanding the self-expanding stent from the compressed configuration to an expanded configuration, wherein during advancing the self-expanding stent out of the elongate member, a diameter of the anisotropic portion surrounding the flared ends of the self-expanding stent in the compressed configuration is greater than the anisotropic portion not surrounding the flared ends of the self-expanding stent in the compressed configuration.

2. The method of claim 1, wherein advancing the self-expanding stent out of the elongate outer member comprises distally advancing the pusher assembly.

3. The method of claim 2, wherein advancing the self-expanding stent further comprises acting on a proximal end of the self-expanding stent.

4. The method of claim 1, wherein advancing the self-expanding stent out of the elongate outer member comprises proximally retracting the elongate outer member and maintaining position of the self-expanding stent using the pusher assembly.

5. The method of claim 1, wherein advancing the self-expanding stent out of the elongate outer member comprises proximally retracting the elongate outer member and distally advancing the pusher assembly.

6. The method of claim 5, wherein proximally retracting the elongate outer member and distally advancing the pusher assembly are at least partially simultaneous.

7. The method of claim 1, wherein advancing the self-expanding stent comprises radially expanding an inwardly tapered distal end of the elongate outer member.

* * * * *